United States Patent [19]
Yamamoto et al.

[11] Patent Number: 5,607,416
[45] Date of Patent: Mar. 4, 1997

[54] DISPOSABLE ABSORBENT PAD

[75] Inventors: Masamitsu Yamamoto; Rumi Yamaki, both of Kawanoe; Hideaki Kitaoka, Funabashi, all of Japan

[73] Assignee: Uni-Charm Corporation, Ehime-ken, Japan

[21] Appl. No.: 321,953

[22] Filed: Oct. 12, 1994

[30] Foreign Application Priority Data

Oct. 15, 1993 [JP] Japan ................................. 5-258719
Dec. 8, 1993 [JP] Japan ................................. 5-307753

[51] Int. Cl.$^6$ .......................... A61F 13/15; A61F 13/20
[52] U.S. Cl. ..................... 604/397; 604/396; 604/385.2; 604/402; 604/393
[58] Field of Search ............................. 604/385.1, 385.2, 604/393–394, 396–397, 400–402

[56] References Cited

U.S. PATENT DOCUMENTS

| | | | |
|---|---|---|---|
| 1,110,674 | 9/1914 | Rosiers | 604/401 |
| 2,871,859 | 2/1959 | Dunn | 604/401 |
| 2,881,761 | 4/1959 | Kenner | 604/401 |
| 3,452,753 | 7/1969 | Sanford . | |
| 4,623,342 | 11/1986 | Ito et al. | 604/385.2 |
| 4,704,115 | 11/1987 | Buell | 604/385.1 |
| 4,846,825 | 7/1989 | Enloe et al. | 604/385.1 |
| 4,940,464 | 7/1990 | Van Gompel et al. | 604/385.2 |
| 5,135,522 | 8/1992 | Fahrenkrug et al. | 604/392 |
| 5,221,277 | 6/1993 | Beplate | 604/394 |
| 5,304,160 | 4/1994 | Igaue et al. | 604/385.2 |
| 5,415,644 | 5/1995 | Enloe | 604/385.1 |
| 5,417,680 | 5/1995 | Kimura et al. | 604/385.2 |

FOREIGN PATENT DOCUMENTS

| | | | |
|---|---|---|---|
| 57-143502 | 9/1982 | Japan . | |
| 0309712 | 11/1955 | Switzerland | 604/401 |
| 2265834 | 10/1993 | United Kingdom | 604/385.1 |

*Primary Examiner*—John G. Weiss
*Assistant Examiner*—Bruce E. Snow
*Attorney, Agent, or Firm*—Lowe, Price, LeBlanc & Becker

[57] ABSTRACT

A disposable absorbent pad comprising a pad member adapted to present a boat-shape under the contractile force of elastic members contained in side flaps, and an elastic support member; longitudinally opposite of the pad member are connected to front and rear sides of the support member by end flaps each comprising top-and backsheets of the pad member and divided in a pair of end flap halves by a slit so as to function as a suspending strap; and the end flap halves are set apart in a V-shape with the slit therebetween as the support member is stretched and contribute to suspend the pad member with high stability.

3 Claims, 7 Drawing Sheets

DISPOSABLE ABSORBENT PAD

BACKGROUND OF THE INVENTION

The present invention relates to so-called disposale absorbent pads, particularly such as incontinence pads or sanitary or menstruation pads, adapted to be used only once and then thrown away.

So far as it is known to the inventors, there are several articles of prior art used as incontinence guards which are partially similar in their constructions to a disposable absorbent pad of the present invention. For example, the specification of U.S. Pat. No. 3,452,753 discloses an article comprising a water-impermeable outer cover (not disposable) designed for elastic fitness around the wearer's waist- and leg-holes and a support attached to the inner side of the cover for a separate absorbent pad and Japanese Laid-Open Patent Application No. 1982-143502 discloses an article comprising an elastically stretchable waist band and straps interconnected to each other so as to form a supporter (not disposable) functioning to support a separate absorbent pad, wherein the supporter surrounds the wearer's legs not completely but partially.

These well known techniques are similar to the invention in that there are provided the straps connected to the elastically stretchable waist band to support the absorbent pad in direct or indirect manner and the basic body or supporter is configured so as to surround the wearer's legs not completely but partially.

There are many other incontinence guard articles of prior art, particularly of disposable type, for example, a disposable incontinence guard article comprising a liquid-permeable topsheet, a liquid-impermeable backsheet, a liquid-absorbent core sandwiched between these two sheets, and elastically stretchable members arranged along waist- and leg-holes and such an article further comprising a separate absorbent pad to be attached to the inner side of the article.

The straps employed by the prior art disclosed in U.S. Pat. No. 3,452,753 appear to be provided for the purpose of assuring a stability with which a pad member of the article can be put on the wearer's body and the straps employed by the prior art disclosed in Japanese Laid-Open Patent Application No. 1982-143502 function only as components of the supporter.

According to the arrangement disclosed in the specification of U.S. Pat. No. 3,452,753, much time and labor would be required to make the article since the straps comprise a combination of the basic component of the article and the separate components. According to the arrangement disclosed in Japanese Laid-Open Patent Application No. 1982-143502, the supporter forms a part of the supporter but a wearer would be bothered with considerably troublesome handling in actual use of the article since the wearer must exactly apply the absorbent pad provided separately of the supporter to the latter. Such arrangement appears to be deficient in stability with which the absorbent pad could be suspended and therefore to be short of reliability with which excretion leakage could be avoided. Furthermore, both of these straps of the prior art have no elastic stretchability and therefore no function for pulling the basic body or supporter up toward the wearer's crotch. Accordingly, the absorbent pad is not maintained in sufficiently close contact with the wearer's crotch so as to prevent leak of excretion from occurring around this zone.

SUMMARY OF THE INVENTION

In view of the problem as has been mentioned above, it is a principal object of the invention to eliminate the problem as has been described by providing means functioning as suspender straps respectively forming parts of longitudinally opposite ends of a pad member so that the pad member may be elastically suspend by such means from an elastic band or a short pant with an elastic waist band.

To achieve the object set forth above, the present invention basically resides in a disposable absorbent pad comprising a pad member for being placed at least in the wearer's crotch and a support member for being placed at least around the wearer's waist, said pad member comprising a liquid-permeable topsheet, a liquid-impermeable backsheet and a liquid-absorbent core sandwiched between these two sheets, wherein said top- and backsheets extend outwardly beyond longitudinally opposite ends as well as transversely opposite side edges of said core to form end and side flaps, respectively, said end flaps are formed with slits bisecting them and extend to the longitudinally opposite ends thereof, said side flaps are provided at least in their outer zones and crotch zones with longitudinally stretchable elastic members by attaching them in their stretched states to said side flaps, then with said elastic members being held in their stretched states, said side flaps are at least partially folded inwards and bonded together at longitudinally opposite ends of these portions to form the pad member, and said support member is connected to the longitudinally opposite ends of said end flaps, respectively.

In an alternative basic embodiment of the invention, said portions of the side flaps folded inwards are further at least partially folded outwards.

In these basic embodiments, said top- and backsheets are preferably made of material having a stretchability at least longitudinally the pad member and thereby the respective end flaps are made stretchable in their longitudinal direction.

In these basic embodiments, said elastic support member may comprise an elastic waist band or a short pant with an elastic waist band.

In actual use of the pad, as the support member is placed with predetermined positioning around the wearer's waist, each pair of adjacent end flap halves are far apart from each other substantially in V-shape owing to the presence of the slit defining this pair and suspends the pad member with high stability. With the end flaps being provided with an appropriate stretchability, the pad member is pulled up against the wearer's crotch and at the same time the outer side edges of the respective side flaps are brought under the effect of the elastic members contained in these outer side edges into close contact with the wearer's crotch, particularly, with the inner sides of respective thighs adjacent the respective groins. When it is desired that the pad member should be more correctly positioned against the wearer's crotch, the pad member may be held by the hand, then pulled down against a tensile force of the end flaps and released, whereupon the pad member will be automatically brought back against the wearer's crotch under the contractile force of the end flaps. Obviously, such operation may be repeated, if necessary.

With the pad member correctly placed on the wearer's body in this manner, the side flaps are erected by contraction of the elastic members contained therein against the wearer's skin, thus generally presenting a boat-shape having a substantially U- or inverted $\Omega$-shaped cross-section and a substantially bow-shaped longitudinal section, so that the side flaps may completely receive and guide liquid excretion to the core where the excretion is absorbed and held.

BRIEF DESCRIPTION OF THE DRAWINGS

The invention will be described more in detail by way of example in reference with the accompanying drawings, in which.

PREFERRED EMBODIMENTS OF THE INVENTION

Figure 1:
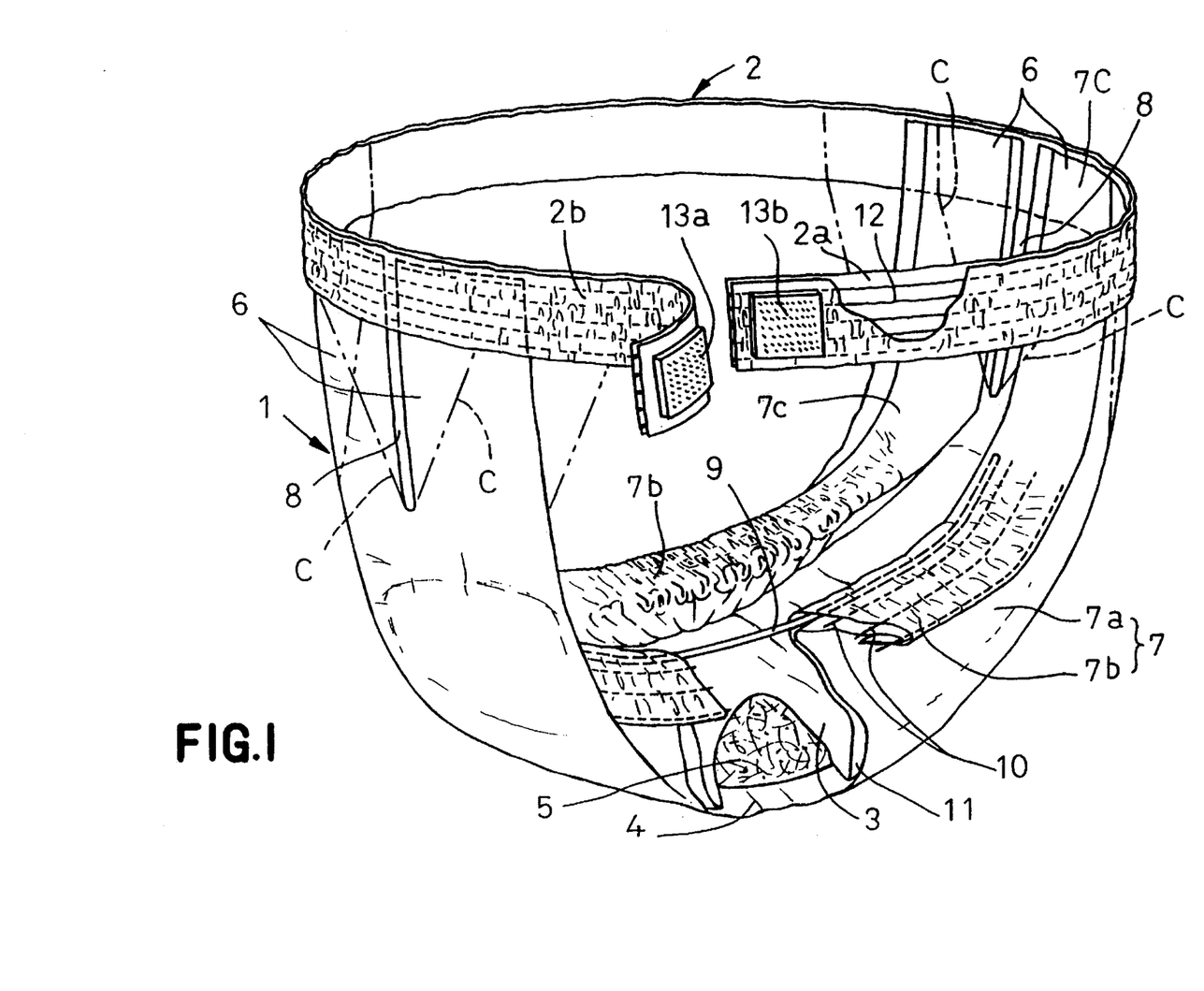
FIG. 1 is a partially broken-away perspective view showing the invention embodied in the form of an incontinence pad as developed for actual use.
Figure 2:
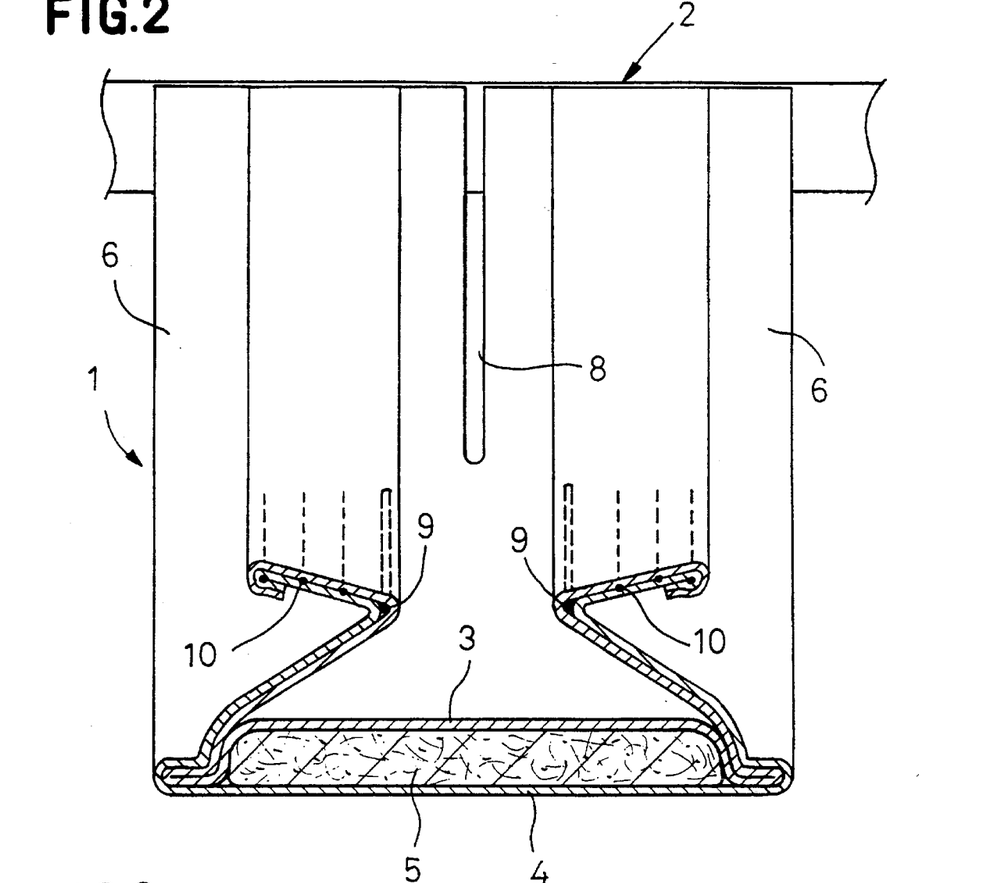
FIG. 2 is a sectional view of a pad member taken in the middle of its length.

Referring to FIGS. 1 and 2, a pad of the invention generally comprises a pad member 1 and an elastic waist band 2 as a support member, formed separately of the pad member 1.

The pad member 1 comprises a liquid-permeable topsheet 3, a liquid-impermeable backsheet 4, a relatively small and narrow liquid-absorbent core 5 sandwiched between these two sheets 3, 4, and end and side flaps 6, 7 comprising portions of the top- and backsheets 3, 4 extending outwards beyond longitudinally opposite ends and laterally opposite side edges of the core 5, respectively, and bonded together by bonding means such as ultrasonic welding, heat welding or adhesive. When a smooth and slippery film such as a plastic sheet (not shown) is used as the backsheet 4, the outer surface of the backsheet 4 may be laminated with a non-woven fabric.

Each end flap 6 is provided in the middle transversely thereof with a slit 8 extending to its outer end. The end flap 6 preferably has an appropriate stretchability. To achieve this, the top- and backsheets 3, 4 may be made of materials having the stretchability at least longitudinally of the pad member 1 or, as will be described later, elastic members 9, 10 may be continuously arranged so as to be contained not only in the side flaps 7 but also in the end flaps 6 (see FIG. 5).

Each side flap 7 contains at least over a section in its outer zone extending between a line approximately defining the middle of its whole width and the outermost edge thereof, destined to be applied against the wearer's crotch, longitudinally stretchable elastic members 9, 10 bonded in their stretched state between the top- and backsheets 3, 4 by adhesive of suitable type. The elastic member 9 comprises a single elastic element having a relatively high stretching stress while the elastic member 10 comprises a plurality of elastic elements arranged in parallel one to another and having a relatively low stretching stress. These elastic members 9, 10 may continuously extend to points adjacent the outer end of the end flap 6. Each side flap 7 is folded inwards along a line 11 adjacent the outer side edge of the core 5, then the portion thus folded inwards is partially folded outwards along a line defined adjacent the elastic member 9 and longitudinally opposite ends 7c of the respective folded portions 7a, 7b are bonded by means of ultrasonic welding, heat welding, adhesive or the like to the portion of the topsheet 3 overlying the core 5.

So far as the pad is intended to be used exclusively for continence guard, the pad member 1 except the end flaps 6 may be dimensioned so as to cover the urinary organs and the periphery thereof or, to look at, to be perceptibly larger than a usual memstruation pad or napkin. The pad member 1 except the end flaps 6 may be dimensioned to cover not only the urinary organs and the periphery thereof but also the anus and periphery thereof, if necessary.

The pad member 1 of the foregoing arrangement has the side flaps 7 risen primarily by the contractile force of the elastic member 9 against the wearer's skin, generally presenting a boat-shape having a substantially U-shaped or inverted Ω-shaped cross-section and a substantially bow-shaped longitudinal section. The folded portions 7a, 7b of each side flap 7 are inwardly collapsed in completely flat states as the pad member 1 is subjected to a tension exerted thereon in the longitudinal direction. The pad member 1 thus flattened may be longitudinally folded to be compactly packaged.

Figure 3:
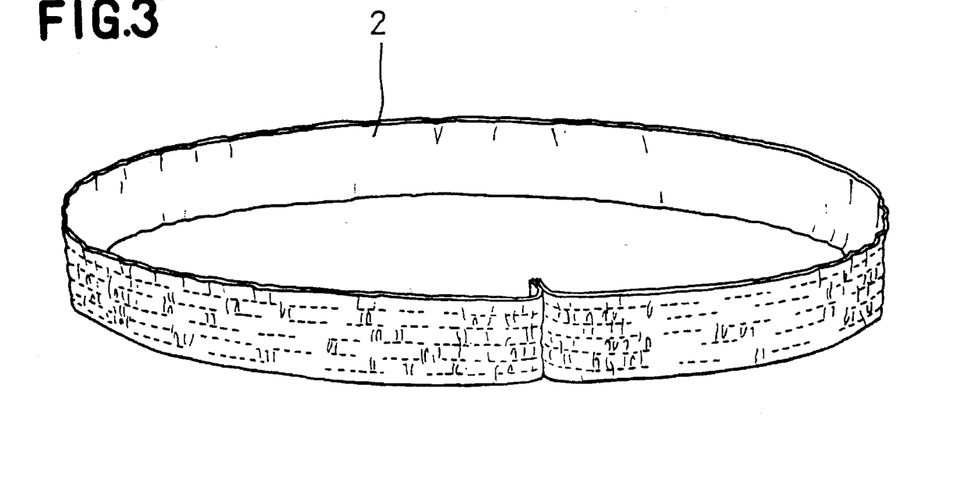
FIG. 3 is a perspective view showing an alternative embodiment of a waist band as elastic support member.

The waist band 2 comprises a pair of narrow sheets 2a, 2b and a plurality of elastic members 12 extending longitudinally and spaced in parallel one from another transversely of the waist band 2, wherein these elastic members 12 are bonded in their longitudinally stretched states between the narrow sheets 2a, 2b by adhesive of suitable type. The waist band 2 has a stretchability significantly higher than the stretchability presented by the end flaps 6 of the pad member 1. Alternatively, the waist band 2 may comprise the other material such as a conventional elastic tape comprising a fabric woven with elastic threads. The waist band 2 presents, when the pad has been placed around the wearer's waist and excretion has been absorbed in the pad member 1, a stretching stress sufficient to prevent the pad member 1 from slipping down due to the load of the pad member 1 thus holding excretion absorbed therein plus the stretching stress of the end flaps 6. Longitudinally opposite ends of the waist band 2 are provided on inner and outer surfaces with fastener means 13a, 13b of well known art, for example, Velcro (Trademark) adapted to be engaged with each other. As will be apparent to those skilled in the art, one side of the waist band 2 may comprise fibers which are engageable with projecting loops of the one Velcro fastener 13a to eliminate a demand for the other Velcro fastener 13b. It is also possible to employ fastener means of any other type such as the conventional tape fastener applied with pressure-sensitive adhesive. Alternatively, the longitudinally opposite ends of the waist band 2 may be arranged so as not to be detachably fastened together as shown by FIG. 3. It is also possible to provide the waist band 2 of endless fashion already formed in a step of its fabrication, though not shown.

With the pad member 1 being placed against the wearer's crotch, the fastener means 13a, 13b of the waist band 2 are located so as to leave the abdominal center free, and the end flaps 6 of the pad member 1 are bonded with their respective outer ends by means of ultrasonic welding, heat welding, adhesive or the like to the inner surface of the waist band 2 at appropriate positions unoccupied by the fastener means 13a, 13b.

Figure 4:
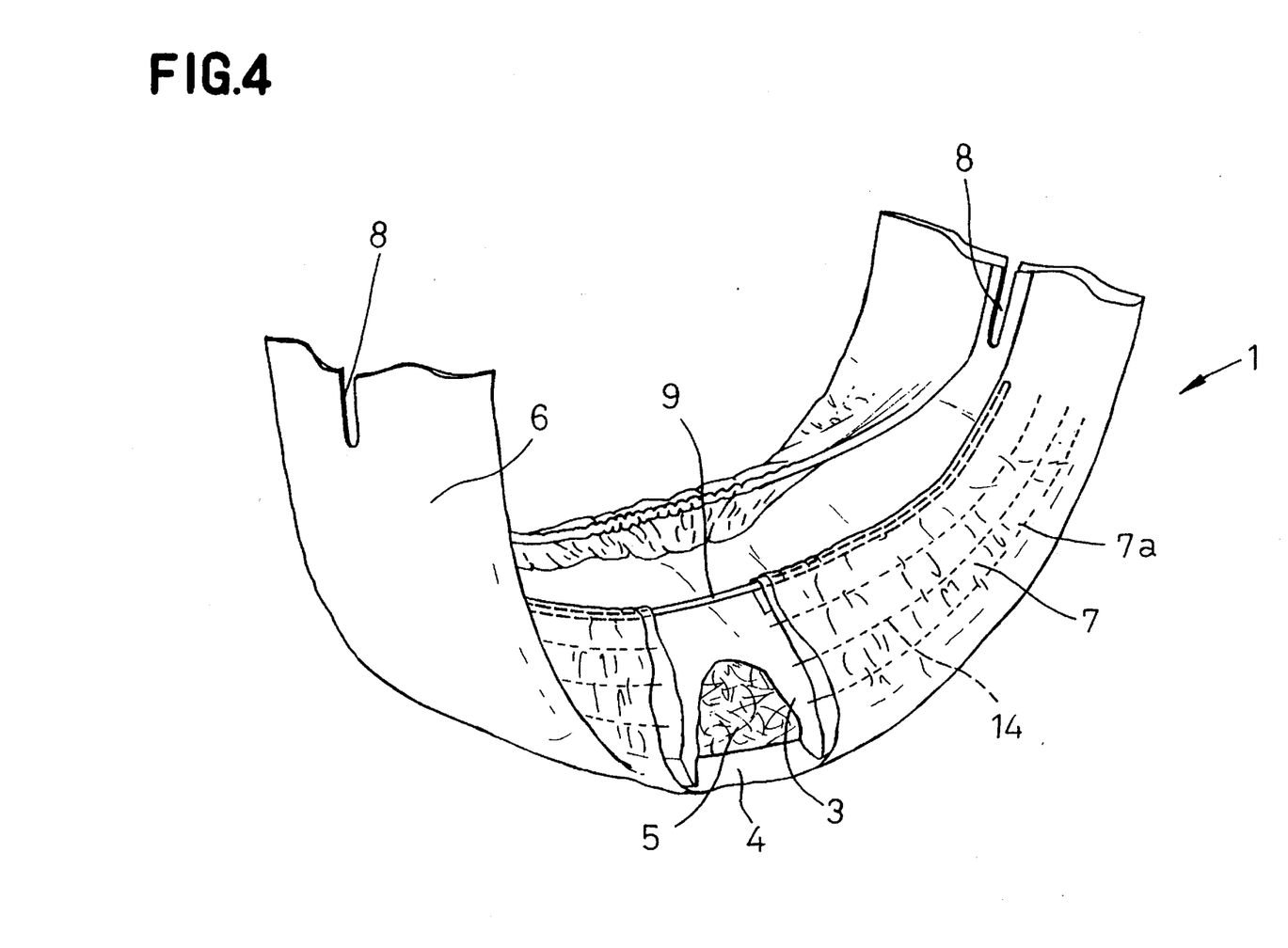
FIG. 4 is a view similar to FIG. 1 but showing an alternative embodiment of the pad member.

The pad member 1 of FIG. 4 is similar to the pad member 1 of FIGS. 1 and 2 except that each side flap 7 is not provided with a portion corresponding to said outwardly folded portion 7b of the previous embodiment and has a portion 7a corresponding to the inwardly folded portion 7a of the previous embodiment is provided with an elastic member 14.

The pad member 1 may be made of the same materials as usually used for disposable diapers, menstruation pads or napkins and the like. For example, the topsheet 3 may be made of a nonwoven fabric, the backsheet 4 may be made of a plastic film and the core may be made of fluff pulps mixed with high absorption polymer powders. The waist band 2 may be made of, for example, soft sheets such as nonwoven fabric sheets having elastic threads sandwiched therebetween in the well known manner.

Figure 5:
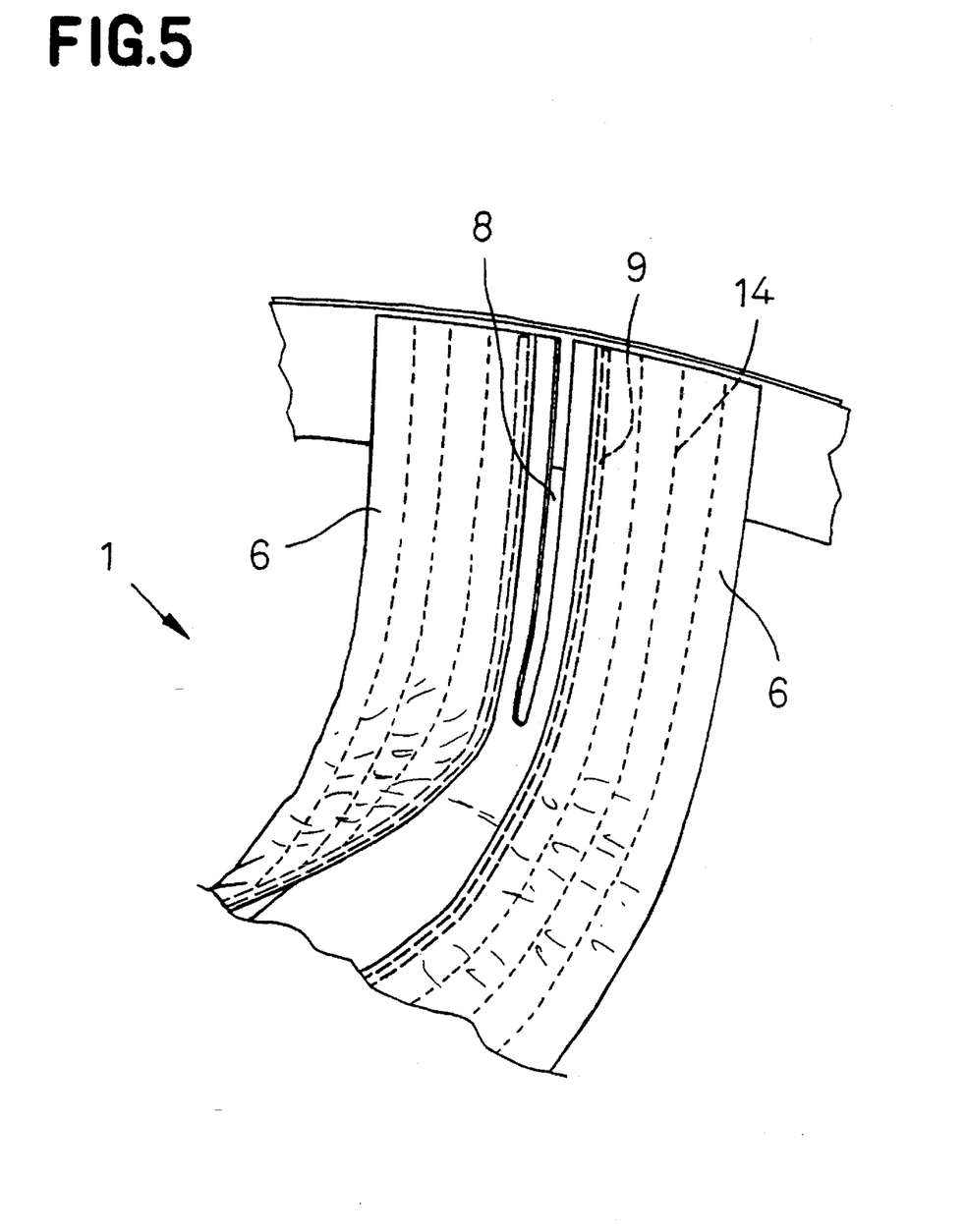
FIG. 5 is a view similar to FIG. 1 but showing further another embodiment of the pad member having elastic members continuously extend in the side and end flaps thereof.

The pad member 1 of FIG. 5 corresponds to the pad member 1 of FIG. 4 in which the elastic members 9, 10 contained in the side flaps 7 extend further into the respective end flaps 6 in order to provide these end flaps 6 also with longitudinal stretchability. As will be readily understood, the pad member 1 of FIG. 1 also may be modified in the same manner so that the elastic member 9, 10 extend further into the respective end flaps 6 and thereby these end flaps 6 also are provided with the stretchability.

With the absorbent pad of the invention put on the wearer's body, the waist band 2 is stretched longitudinally or circumferentially thereof and, as indicated by two-dot-chain lines C in FIG. 1, each pair of adjacent end flap halves 6 are set apart owing to the presence of the associated slit 8 from each other substantially in a V-shape so as to suspend the pad member 1 with high stability. The side flaps 7 are elastically brought into close contact with the wearer's crotch and the portions of the respective side flaps 7 extending along the respective elastic members 9 are elastically pressed against the wearer's groins. In this state, the pad member 1 presents substantially a boat-like shape so that excretion can be reliably received, absorbed and held by the pad member 1 without any apprehension that the excretion once received by the pad member 1 might leak outwards.

When the absorbent pad of the invention is used as means for continence guard, the embodiment of FIG. 1 is suitable for common use by men and women while the embodiment of FIG. 4 is suitable for men's exclusive use. The embodiment of FIG. 1 is particular effective to avoid the excretion leakage since this embodiment has the outwardly folded portions 7b destined to be elastically brought into surface contact with inner sides of the wearer's thighs over a relatively wide area. The embodiment of FIG. 1 is suitable also as the women's sanitary or menstruation pad and will be suitable as the sanitary or menstruation pad for women having disabled bodies if the waist band 2 is formed in endless fashion.

Figure 6:
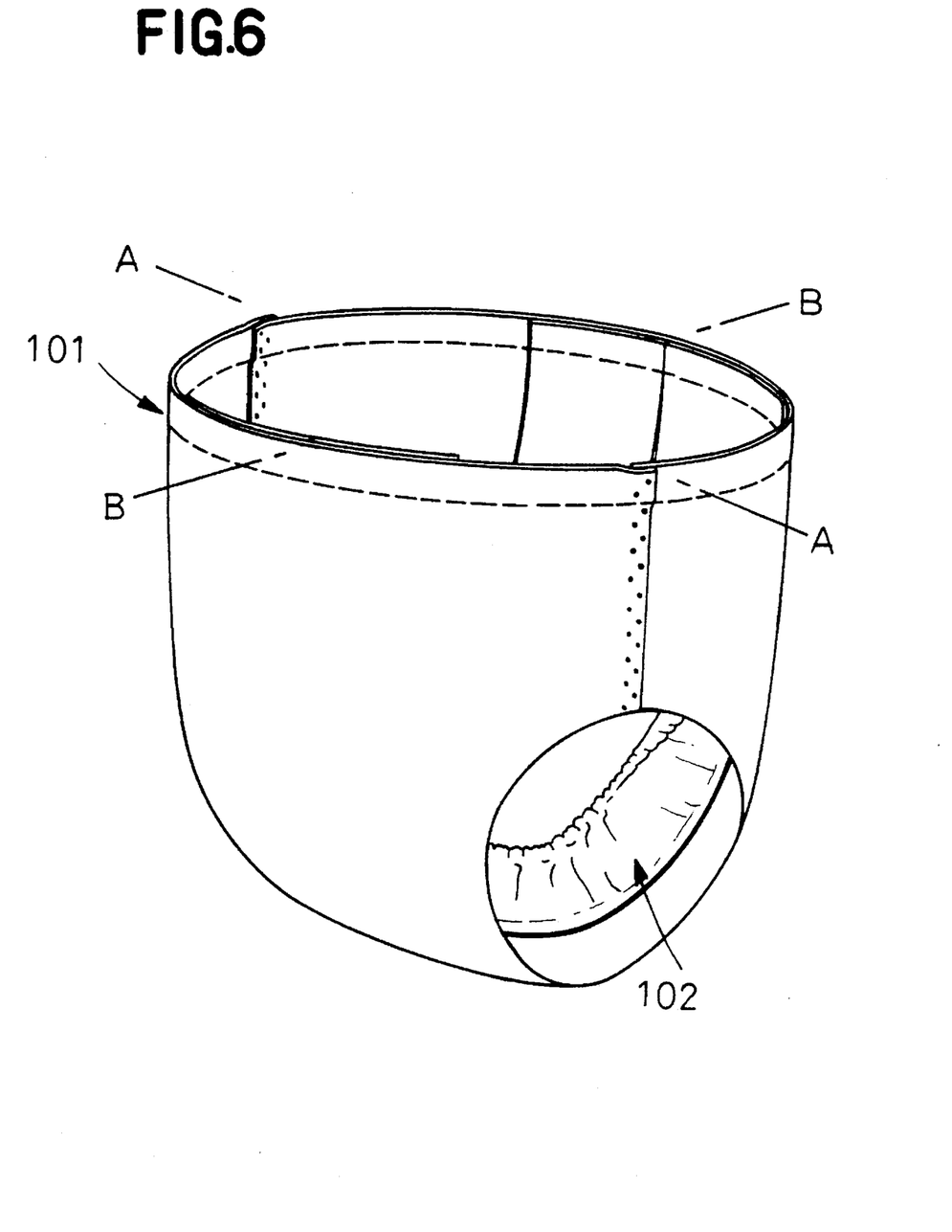
FIG. 6 is a perspective view showing a disposable pant as another embodiment of the invention.
Figure 7:
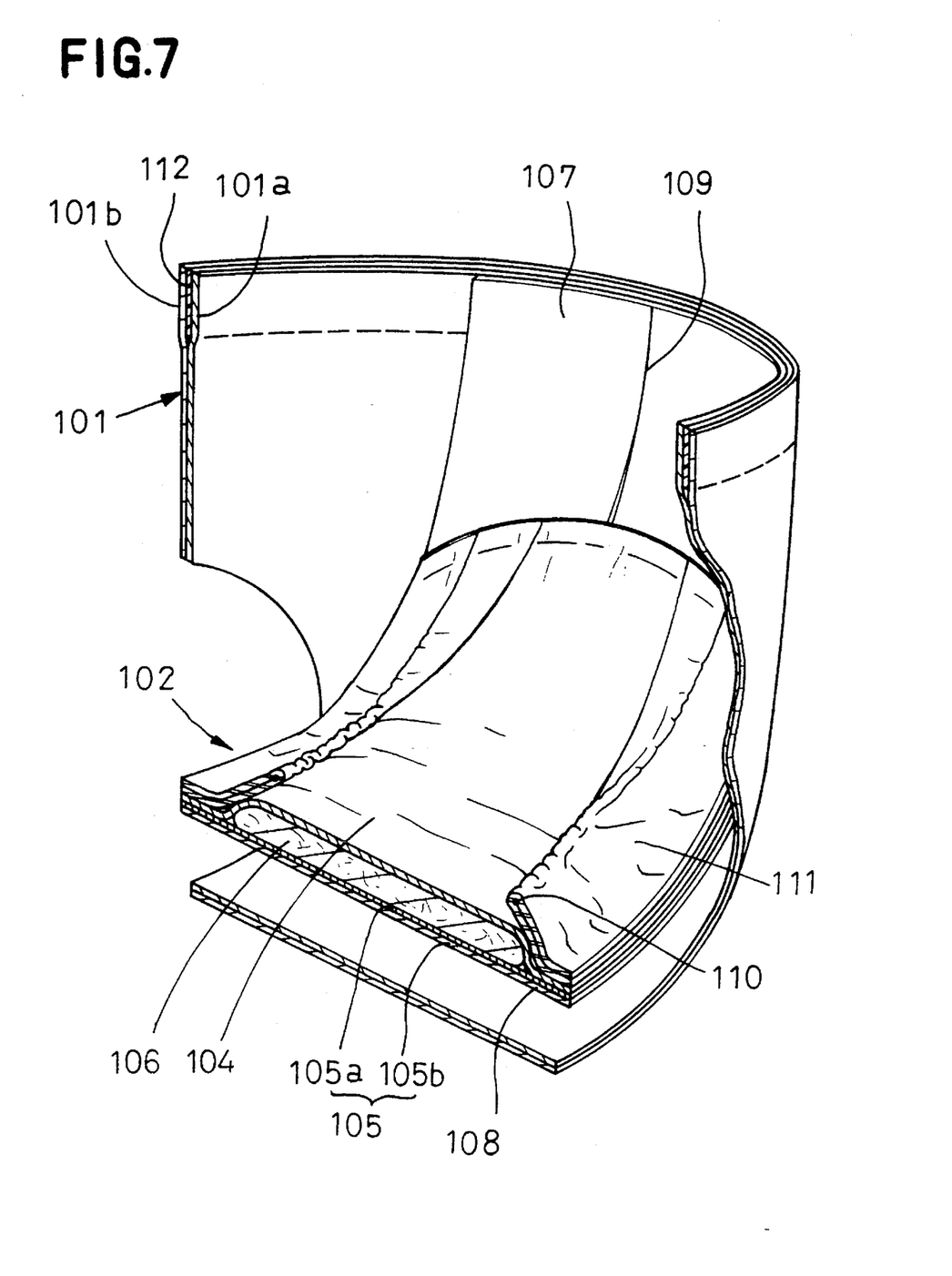
FIG. 7 is a perspective view showing the same pant, partially in a section taken along a line A—A in FIG. 6.
Figure 8:
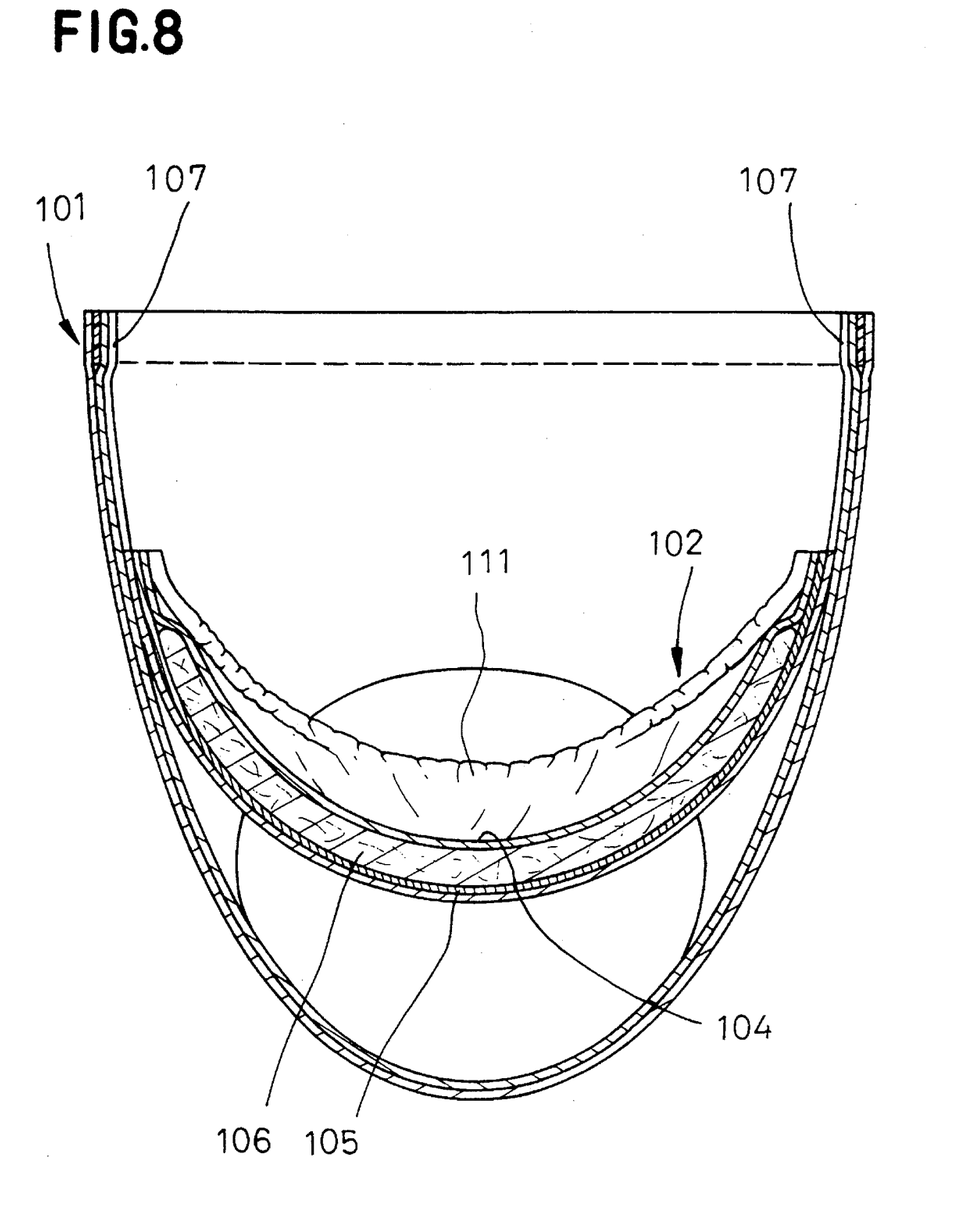
FIG. 8 is a sectional view taken along a line B—B in FIG. 6.

Referring to FIGS. 6 through 8, a disposable absorbent pad as another embodiment of the invention generally comprises a pant member 101 as a support member and a pad member 102.

The pant member 101 comprises front and rear bodies bonded together along transversely opposite side edges thereof by means of ultrasonic welding, heat welding, adhesive or the like so as to form, in the well known manner, a waist-hole and a pair of leg-holes. The pant member is made of material being stretchable in length and width, and said waist- and leg-holes are so dimensioned that these holes may closely fit around the wearer's waist and legs, respectively, under the contractibility inherent in the material.

The pad member 102 comprises a liquid-permeable topsheet 104, a liquid-impermeable backsheet 105 and a relatively small and narrow liquid-absorbent core 106 sandwiched between these two sheets 104, 105, wherein the backsheet 105 extends outwards beyond longitudinally opposite ends of the core 106 while the top- and backsheets 104, 105 extend outwards beyond transversely opposite side edges of the core 106 to form end flaps 107 and first side flaps 108 and, in the respective side flaps, the top- and backsheets 104, 105 are bonded together along their side edges.

Each end flap 107 is provided with a slit 109 transversely dividing it in two halves and extending to a longitudinal end of this end flap 107. The end flap 107 preferably has an appropriate stretchability and, to achieve this, the backsheet 105 may be made of material having a stretchability at least longitudinally of the pad member 102 or a suitable elastic member may be attached, in its stretched state, to the end flap 107.

The pad member 102 further comprises second side flaps 111 each folded in two and provided with an elastic member 110 attached in its stretched state to the inner surface of the flap along the folding line. These second flaps 111 are placed upon the respective first side flaps 108 and bonded thereto along side edges opposite to said folding lines, respectively. Each second side flap 111 has longitudinally opposite ends collapsed outwards and bonded together by means of ultrasonic welding, heat welding, adhesive or the like. Accordingly, the second side flaps 111 are biased by the contractibility of the respective elastic members 110 to rise. Alternatively, the second side flaps 111 may be formed by extensions of the respective first side flaps 108, though not shown.

To suspend the pad member of the foregoing construction, the longitudinally opposite ends of the respective end flaps 107 are bonded to the inner surface of the pant member 101 adjacent the waist line by means of ultrasonic welding, heat welding, adhesive or the like in such a manner that, over the crotch zone, a gap is formed between the bottom surface of the pad member 102 and the top surface of the pant member 101.

The pant member 101 may be made from a laminate of a stretchable nonwoven fabric 101a and stretchable and a moisture-permeable plastic film 101b and include an elastic member 112 attached thereto circumferentially along the waist line. It should be understood that the elastic member 112 has a stretching stress higher than that of said laminate. For the pad member 102, the backsheet 105 may be made from a laminate of a stretchable nonwoven fabric 105a and a stretchable and moisture-permeable plastic film 105b, the topsheet 104 may be made from a nonwoven fabric, the core 106 may be made from fluff pulps mixed with high absorption polymer powders, and the second side flaps 111 may be made from a water repellent nonwoven fabric.

What is claimed is:

1. A disposable absorbent pad comprising:

a pad member for being placed at least in the wearer's crotch, said pad member comprising a liquid-permeable topsheet, a liquid-impermeable backsheet and a liquid-absorbent core sandwiched between said topsheet and said backsheet;

said topsheet and said backsheet extending outwardly beyond longitudinally opposite ends of said core to form end flaps, said end flaps being formed with slits bisecting and extending to the longitudinally opposite ends thereof;

said topsheet and said backsheet extending outwardly beyond transversely opposite side edges of said core to form side flaps, said side flaps are provided with longitudinally stretchable elastic members attached in their stretched states to said side flaps, a portion of each said side flaps is partially folded inwards with said elastic members being held in their stretched states and bonded together at longitudinally opposite ends of these folded portions; said folded portions being further partially folded outwards; and a support member for being placed at least around the wearer's waist and connected to the longitudinally opposite ends of said end flaps, the support member being elastically stretchable, the end flaps being disposed immediately adjacent one another when the support member is in the unstretched state and being spread apart from one another to form a "V" when the support member is in the stretched shape.

2. A disposable absorbent pad comprising:

a pad member for being placed at least in the wearer's crotch, said pad member comprising a liquid-permeable topsheet, a liquid-impermeable backsheet and a liquid-absorbent core sandwiched between said topsheet and said backsheet;

said topsheet and said backsheet extending outwardly beyond longitudinally opposite ends of said core to form end flaps, said end flaps being formed with slits bisecting and extending to the longitudinally opposite ends thereof;

said topsheet and said backsheet extending outwardly beyond transversely opposite side edges of said core to form side flaps, said side flaps are provided with longitudinally stretchable elastic members attached in their stretched states to said side flaps, said side flaps are partially folded inwards with said elastic members being held in their stretched states and bonded together at longitudinally opposite ends of these folded portions; and a support member for being placed at least around the wearer's waist and connected to the longitudinally opposite ends of said end flaps, the support member being elastically stretchable, the end flaps being disposed immediately adjacent one another when the support member is in the unstretched state and being spread apart from one another to form a "V" when the support member is in the stretched shape;

wherein said elastic members are arranged so as to extend further into said end flaps and thereby said end flaps are also provided with a longitudinal stretchability.

3. A disposable absorbent pad, comprising:

a pad member adapted to be placed at least in the wearer's crotch, said pad member including a liquid-permeable topsheet, a liquid-impermeable backsheet and a liquid-absorbent core sandwiched between said topsheet and said backsheet;

said topsheet and said backsheet extending outwardly beyond longitudinally opposite ends of said core to form end flaps, said end flaps being formed with slits substantially bisecting and extending to the longitudinally opposite ends thereof;

said topsheet and said backsheet extending outwardly beyond transversely opposite side edges of said core to form side flaps, said side flaps are provided with longitudinally stretchable elastic members attached in their stretched states to said side flaps, said side flaps are partially folded inwards with said elastic members being held in their stretched states and bonded together at longitudinally opposite ends of these folded portions; and a support member for being placed at least around the wearer's waist and connected to the longitudinally opposite ends of said end flaps, the support member being elastically stretchable, the end flaps being disposed immediately adjacent one another when the support member is in the unstretched state and being spread apart from one another to form a "V" when the support member is in the stretched shape;

wherein said elastic members include an elastic member extending adjacent the outermost edge of said inwardly folded portion of each side flap and an elastic member disposed inwardly therefrom, said elastic member extending adjacent the outermost edge of said inwardly folded portion of each side flap has a stretching stress higher than that of said other elastic member.

* * * * *